United States Patent [19]
Arbogast et al.

[11] Patent Number: 6,063,125
[45] Date of Patent: May 16, 2000

[54] SUSPENSION/ALIGNMENT FOR PROSTHETIC LIMBS

[75] Inventors: Robert E. Arbogast; James W. Capper, both of Mt. Sterling; James M. Colvin, Hilliard, all of Ohio

[73] Assignee: Ohio Willow Wood Company, Mount Sterling, Ohio

[21] Appl. No.: 08/801,580

[22] Filed: Feb. 14, 1997

[51] Int. Cl.[7] ................................. A61F 2/62; A61F 2/80
[52] U.S. Cl. ................................................ 623/34; 623/38
[58] Field of Search .................. 623/33, 34, 38, 623/27, 57, 37

[56] References Cited

U.S. PATENT DOCUMENTS

| | | | |
|---|---|---|---|
| 980,457 | 1/1911 | Toles | 623/37 |
| 2,654,294 | 10/1953 | Morden . | |
| 2,790,180 | 4/1957 | Hauser | 623/34 |
| 3,007,176 | 11/1961 | Hafner | 623/26 |
| 3,422,462 | 1/1969 | Finnieston . | |
| 5,013,325 | 5/1991 | Rennerfelt . | |
| 5,139,523 | 8/1992 | Paton et al. | 623/37 |
| 5,376,129 | 12/1994 | Faulkner et al. | 623/33 |
| 5,425,782 | 6/1995 | Phillips . | |
| 5,662,715 | 9/1997 | Slemker | 623/36 |
| 5,702,489 | 12/1997 | Slemker | 623/34 |
| 5,728,170 | 3/1998 | Becker et al. | 623/37 |

FOREIGN PATENT DOCUMENTS

| | | | |
|---|---|---|---|
| 0 765 646 A1 | 4/1997 | European Pat. Off. | 623/34 |
| 1308325 A1 | 5/1987 | U.S.S.R. | 623/33 |
| 778563 | 7/1957 | United Kingdom | 623/34 |

*Primary Examiner*—David H. Willse
*Attorney, Agent, or Firm*—Oblon, Spivak, McClelland, Maier & Neustadt P.C.

[57] ABSTRACT

A prosthetic limb suspension system includes a socket part having a cavity into which a residual limb may be introduced, a distal adaptor secured at a distal end of the socket part, and an air valve mounted to the distal adaptor and communicating with the cavity so as to selectively permit air flow to or from the cavity.

20 Claims, 6 Drawing Sheets

SUSPENSION/ALIGNMENT FOR PROSTHETIC LIMBS

BACKGROUND OF THE INVENTION

1. Field of the Invention

The present invention relates to a prosthetic limb system which suspends a prosthetic limb from a residual limb stump. More particularly, it relates to a distal adaptor incorporating an air valve, or a simplified distal adaptor for use with thermoplastic sockets.

2. Description of the Related Art

It has been known to suspend a prosthetic limb from a residual limb by use of suction. In such a case, the prosthetic limb is suspended using a socket part having a proximal end shaped as a cavity into which the limb stump may be inserted. The inserted residual limb forms an airtight seal with the socket part to hold the socket part on the residual limb by suction. Air is vented from between the residual limb and the socket part during insertion of the limb and is prevented from re-entering through the socket part to maintain the vacuum. Conventional prosthetic socket parts therefore have an air valve which permits the expulsion of the air between the end of the residual limb and the socket part.

Figure 1:
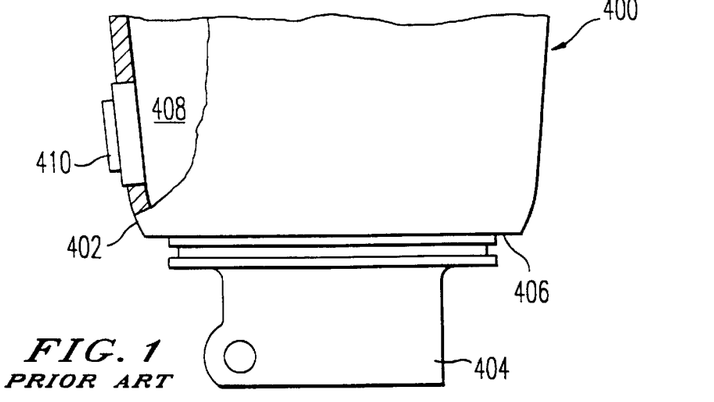
FIG. 1 is a front view, partially cut away, of a conventional laminated socket part incorporating a valve.

Referring to FIG. 1, a conventional prosthetic limb suspension system 400 has a socket part 402 which mounts a distal adapter 404 at its distal end 406. The distal adaptor is used to clamp a pylon or other prosthetic part to the socket part. The interior 408 of the socket part is shaped to accept a residual limb and form a seal therewith so that withdrawal of the residual limb is prevented by suction. A valve 410 is mounted in a sidewall of the socket part to permit the expulsion of air during insertion of the residual limb into the socket part.

The conventional systems, however, suffer from a number of shortcomings. One is that air is often trapped within the socket part between the valve 410 and the distal end of the socket. That is, the residual limb may cover and block the valve 410 before all of the air has been discharged during the insertion of the residual limb into the socket part, thereby reducing the suction hold effect and user comfort.

Another common problem with prosthetic limb suspension systems using air expulsion valves is that the valves are easily clogged and must be cleaned or replaced at regular intervals. With current designs, a choice must be made between ease of maintenance and optimal appearance. The valve can be made to be easily accessible for maintenance by creating an opening through the cosmetic cover of the prosthetic limb. However, most users do not like to have any discontinuities in the cosmetic finish. The other alternative with current designs is to "bury" the valve in the cosmetic cover. This makes maintenance of the valve difficult and time consuming because the cosmetic cover must be removed and later repaired or replaced.

Yet another common problem with conventional prosthetic limb suspension systems is their complexity, particularly the need in many cases to provide a two-piece socket part including an inner socket. Prosthetic socket parts are normally either laminated with a thermosetting resin or molded with a thermoplastic sheet or cone. Laminated sockets are generally of single wall construction and thermoplastic sockets are often of double wall construction. When laminating with a thermosetting resin, the distal adaptor is usually a single piece adaptor which is laminated directly to the distal end of the socket part. If using suction suspension, a valve can be laminated directly into the wall of the socket. When molding with a thermoplastic material, on the other hand, the distal adaptor generally consists of an internal piece and an external piece which are clamped together with the distal end of an outer thermoplastic socket part sandwiched between them. A second, inner thermoplastic socket part is therefore necessary to fit inside this outer thermoplastic socket part having the distal adaptor clamped thereto.

It is conventionally not considered possible to use a single thermoplastic socket part incorporating an air valve, for a number reasons. First, since the distal adaptor is attached to the distal end of the outer socket part by fastening the internal end external pieces of the distal adaptor with fasteners which pass through the wall of the outer socket part, it is difficult to provide an adequate seal where the fasteners pass through the outer socket wall. The inner socket part is therefore necessary to aid in sealing.

Second, the proximal surface of the internal adaptor piece of current distal adaptors would not be comfortable for contact with the residual limb, and so the inner socket part is required to increase user comfort.

Third, the thermoplastic property requirements for the mounting of the distal adaptor to the socket part are different from those for the incorporation of a valve into the socket part. That is, in order to provide adequate structural rigidity for attaching the distal adaptor, the thermoplastic must be relatively thick and rigid. On the other hand, the valves are conventionally molded directly into the wall of the socket part, and so the thermoplastic should be relatively thin and flexible to conform to the contours of the valves and provide an adequate seal. The designs of the valves are such that the relatively thick thermoplastic required for the attachment of the distal adaptor is too thick and rigid to provide sufficient contouring around the valve for a good seal.

The two separate socket parts, an inner socket part made from a thin flexible thermoplastic and an outer socket part made from a thicker, more rigid thermoplastic is a conventional technique for addressing this problem. However, the double wall socket system having separate inner and outer socket parts adds weight to the prosthesis and increases the labor costs in the fabrication of the prosthesis.

SUMMARY OF THE INVENTION

It is an object of the present invention to overcome the aforementioned shortcomings in the conventional prosthetic limb systems.

It is a further object of the present invention to provide a prosthetic distal adaptor having an air valve providing a reliable suction hold.

It is a further object of the invention to provide a prosthetic limb system having an easily maintained air valve and filter.

It is a further object of the present invention to provide a prosthetic limb system with a single wall thermoplastic socket.

According to one feature of the present invention, the above and other objects are accomplished by a distal adaptor for securement to a distal end of a socket part having a cavity into which a residual limb may be introduced, and having an adaptor part for securing the socket part to a prosthetic limb, and an air valve mounted to the distal adaptor and communicating with the cavity so as to selectively permit air flow to or from the cavity. Since the air valve is in the distal adaptor, it is at the distal-most part of the socket part and so will not be blocked so as to leave trapped air upon insertion of the residual limb in the socket part.

Preferably, a filter positioned for filtering air passing through said air valve from said cavity is mounted in the distal adaptor. It is readily accessible for maintenance from the interior of the socket part.

The air valve may be a one way valve mounted in a bore of the adaptor and permitting air flow from the cavity, or a two way air valve mounted in a bore of the adaptor and having a manually actuatable air release.

The adaptor may be a pyramid adaptor, a pyramid receiver adaptor, a pylon clamp adaptor, or any other adaptor which interfaces with the prosthetic limb.

According to another embodiment of the invention, a seal member may seal between a seal plate and a socket part, and the seal plate may have a surface which conforms in shape to a residual limb to be inserted into said socket part and may have a valve and/or a filter. An inner socket part is therefore unnecessary.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Several embodiments of the invention will now be described with reference to the attached figures, in which the same or similar parts are referred to using the same reference numerals throughout the several views.

Figure 2A:
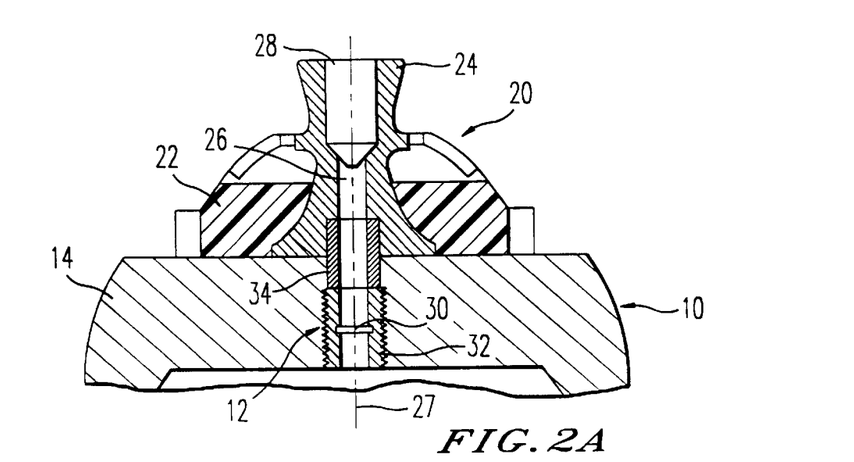
FIGS. 2A and 2B are respectively front or side sectional, and top plan views of a composite, four hole pyramid adaptor incorporating a one-way valve according to the present invention for use in a laminated socket.
Figure 2B:
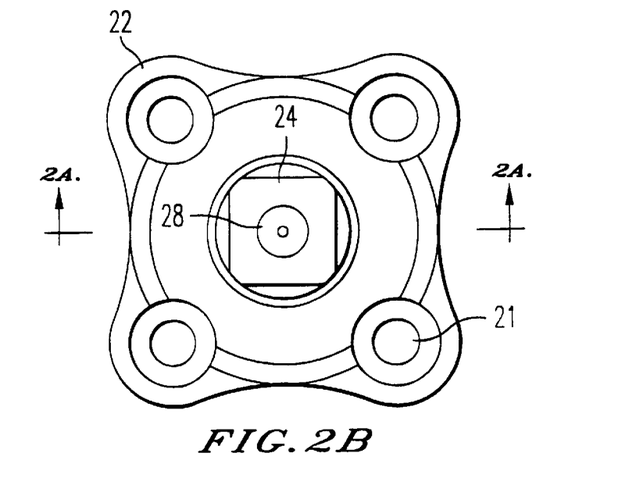

Referring first to FIGS. 2A–2B, a prosthetic limb suspension system comprises two main elements: a socket part 10 and a distal adaptor 20. The socket part 10 is conventional in configuration and may be formed of, e.g., thermoset resin and fiber reinforcement, with the exception that it has a bore 12 extending through the distal end 14.

The distal adaptor 20 in this embodiment is conventional and can correspond to that disclosed in U.S. patent application Ser. No. 08/487,145 filed on Jun. 7, 1995, which is herein incorporated by reference, except as described below. As is conventional, the distal adaptor includes a composite base part 22 which has holes 21 for insertion of screws to hold the distal adaptor onto the distal end of the socket part 10. A metal pyramid type adaptor part 24 has a base embedded in the base part 22. However, unlike the conventional pyramid adaptor, the pyramid adaptor part 24 incorporates a bore 26 extending therethrough. The bore 26 is aligned with the bore 12 of the socket part, and both may be on the longitudinal axis 27 of the suspension system.

A one-way or check valve 28 is mounted in the bore 26 and is constructed so as to permit one-way air flow from the interior of the socket part 10 outwardly through the bores 12 and 26. A micro-screen filter 30 may be mounted in a bushing 32 held, e.g., by screwing, within the aperture 12 of the socket part. A tube 34 fitted in bores 12 and 26 traverses the joint between the socket part 10 and the distal adaptor 20 so as to assure an air tight seal and prevent suction loss at the joint.

Since the check valve is mounted within the distal adaptor 20 which is mounted at the distal end 14 of the socket part, and receives air discharged through the bore 12 at the distal end 14, the entrance of air to the check valve 28 will not be blocked by the residual limb during its insertion into the socket part, and so air will not be trapped within the socket part as can conventionally occur.

Moreover, maintenance to clean or replace a clogged filter can be easily performed by accessing the filter 30 through the interior of the socket part. For example, one can use a tool such as the one identified as 500 in FIG. 4A to unscrew the bushing 32 and remove the filter 30. For this purpose, the end of the tool 500 and the central opening of the bushing 32 within which the end of the tool is fitted may both be non-circular in section.

Figure 3A:
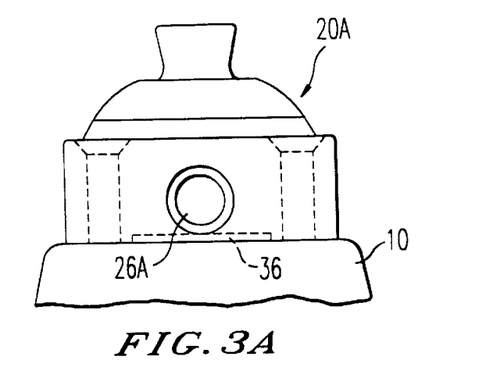
FIGS. 3A, 3B and 3C are respectively side, front sectional and top plan views of a composite four hole pyramid adaptor incorporating a two-way valve sleeve.
Figure 3B:
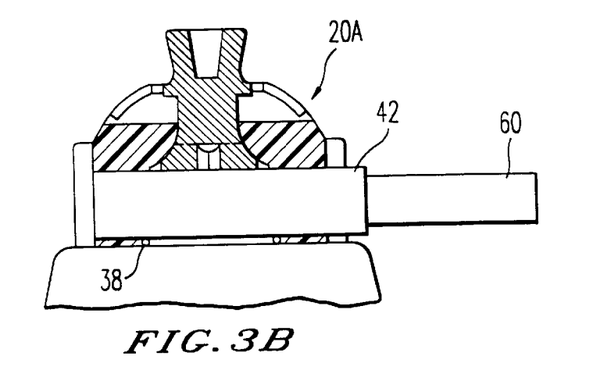
Figure 3C:
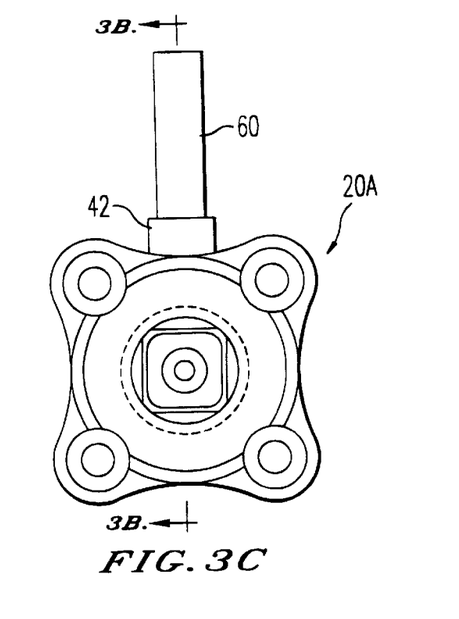

Referring to FIGS. 3A–3C, the parts are the same as those discussed with reference to FIGS. 2A–2B, except as noted below.

The embodiment of FIGS. 3A–3C differs from that of FIGS. 2A–2B primarily in that the suction valve is a two-way valve held in a transversely extending valve sleeve assembly 40 (FIGS. 6A–6B) within a transverse bore 26A of the distal adaptor 20A. The transverse bore 26A communicates with an opening 36 in the bottom of the distal adaptor 20A, the opening 36 communicating with the bore 12 of the socket part 10 when the distal adaptor 20A is mounted to the socket part 10 so that air from the socket part may be discharged via the bore 12, the discharge opening 36 and the two-way valve. An O-ring 38 provides the necessary sealing at the joint between the socket part 10 and the distal adaptor 20A.

Figure 6A:
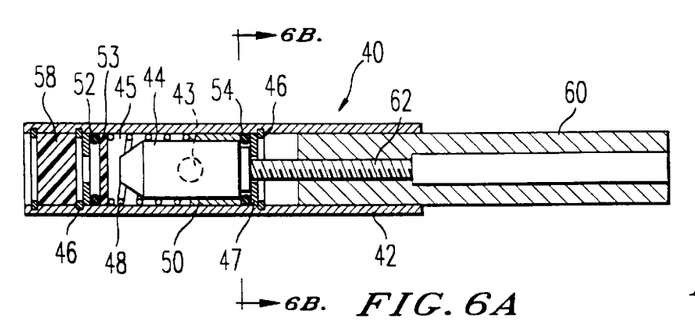
FIGS. 6A and 6B are respectively a front sectional, and end sectional view of a two-way valve sleeve assembly.
Figure 6B:
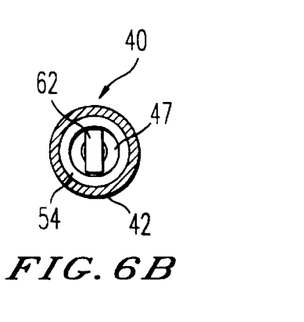

Referring to FIGS. 6A and 6B, the valve sleeve assembly 40 includes a tubular sleeve member 42 which is held within the bore 26A, for example by press fitting. A one-way valve member 44 is normally held at a rest position within the sleeve member 42. The rest position is determined by the spring 48 which presses on a shoulder 50 of the valve member 44 to bias the valve member against an O-ring 54 held by a snap ring 46 via a washer 47. The other end of the spring 48 presses against a seal 53 backed by another washer/O-ring pair 52 positioned by another snap ring 46. A plug 58 closes the end of the sleeve member 42.

The region 45 within the sleeve member 42 surrounding the valve member 44 within the sleeve member 42 is thus sealed at its ends by the O-ring 52 and the end of the valve member 44 pressing against the other O-ring 54. This region is in fluid communication with the opening 36 through a hole 43 in the sleeve member 42 so that any air within the socket part can flow to the region 45 of the valve member and be discharged to the atmosphere through the one-way valve member 44 and past the O-ring 54 as the residual limb is being inserted into the socket part. On the other hand, the spring 48 prevents the valve member 44 from moving away from the rest position (sealing against the O-ring) to permit the backflow of air and relieve the resulting vacuum in the socket part.

The valve member 44 is extended by a screw part 62 which extends past the O-ring 54. A manually actuatable hollow suction relief shaft 60 is threaded on the screw part 62. As seen in FIG. 6B, the screw part may have a rectangular shape so that the discharged air may flow out of the sleeve member 42 through the space between the screw part 62 and the washer 47.

The valve member 44 can be moved away from the rest position by manually moving the hollow suction relief shaft 60 into the sleeve member against the force of the spring 48, thereby releasing the suction within the socket part and permitting easy removal of the prosthetic limb from the residual limb part. Alternatively, a tube could be connected to the end of the sleeve member 42 plugged by the plug 58, which tube could be connected to the bore 12 of the socket part for discharging air through the valve member 44.

Figure 4A:
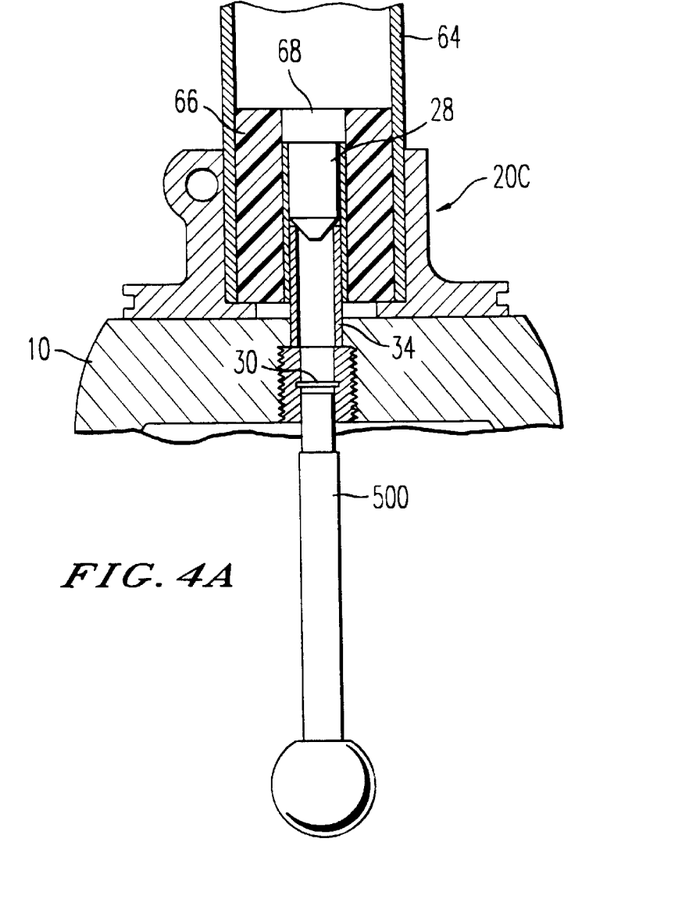
FIGS. 4A and 4B are respectively front sectional and top plan views of an aluminum, four hole pylon adaptor incorporating a one-way valve.
Figure 4B:
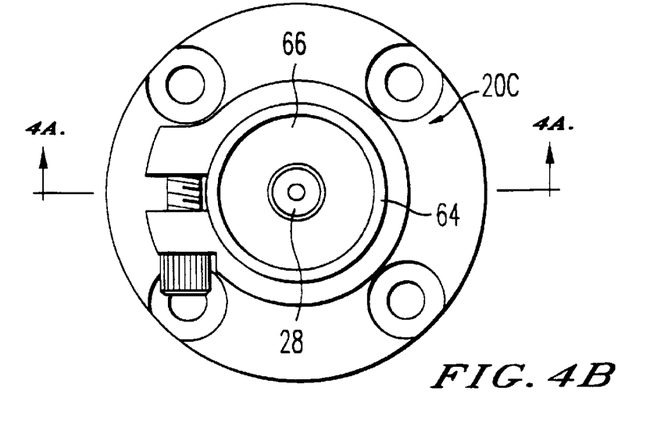

Referring to FIGS. 4A and 4B, the distal adapter may instead be a clamp adapter 20C which clamps a pylon 64. The pylon 64 may be conventional, with the exception that the pylon holds a pylon insert 66 having a bore 68 within which is mounted a one-way valve 28. A tube 34 bridges the joint between the pylon insert 66 and the socket part 10 in the same manner as in FIG. 2A.

Figure 5A:
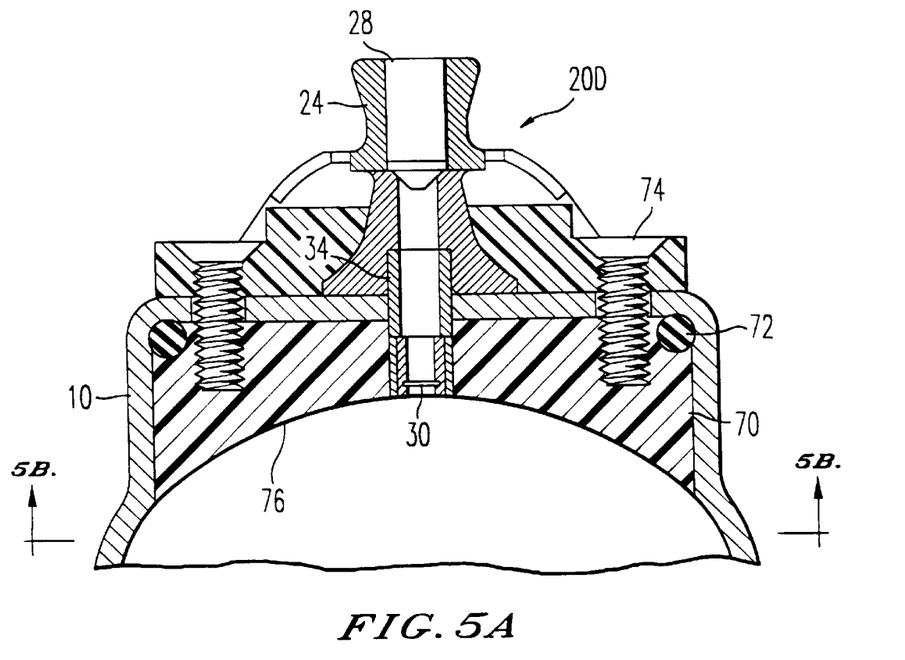
FIGS. 5A and 5B are respectively front sectional and top plan views of a pyramid adaptor incorporating a one-way valve, for use in a thermoplastic socket.
Figure 5B:
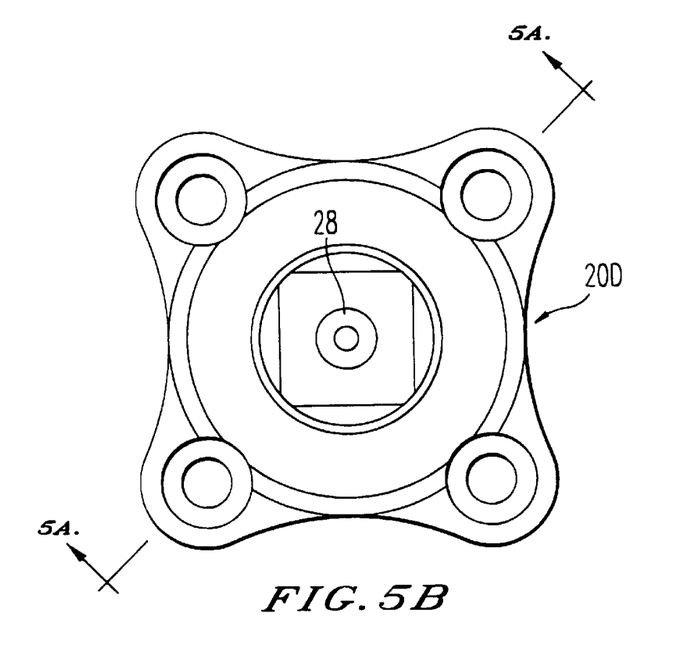

In the embodiment of FIGS. 5A and 5B, the distal adapter 20D is supplemented by a thermoplastic seal plate 70 mounted within the socket part 10 and sealed thereagainst by an O-ring 72. The seal plate 70 is secured to the adapter part by screws 74 and the inner surface 76 of the seal plate is shaped to conform to the end of the residual limb so that the residual limb can be inserted and held within the socket part without discomfort.

Figure 5C:
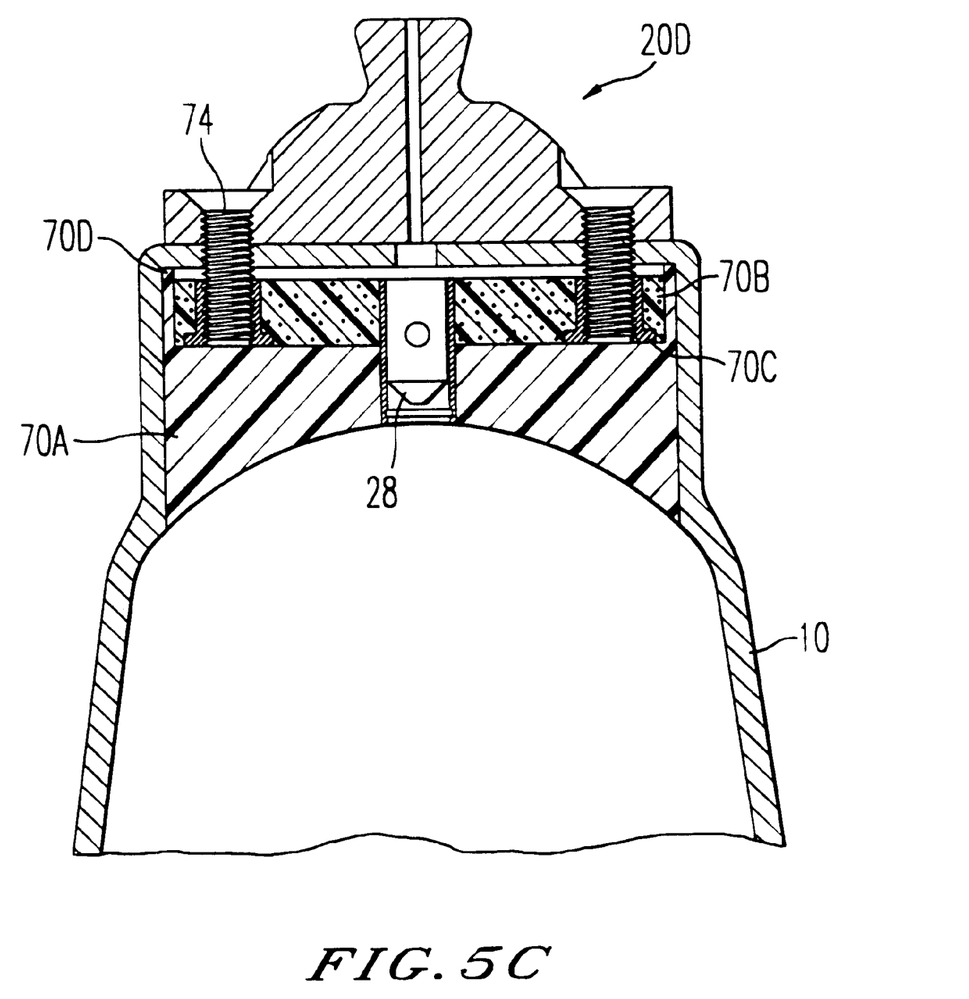
FIG. 5C is a front sectional view of another embodiment of a pyramid adaptor incorporating a one-way valve, for use in a thermoplastic socket.

In the variant of this embodiment shown in FIG. 5C, the seal plate 70A is formed of a resilient material capable of forming a seal, e.g., urethane, and incorporates a hard composite plate 70B having T-nuts 70C molded therein. The screws 74 are threaded into the T-nuts 70C. The sealing function of the O-ring is therefore performed by the edge 70D of the urethane seal plate and the O-ring can be eliminated, as can the tube 34. This variant permits the use of a conventional distal adaptor.

There is no need in this embodiment for an inner socket part. Since the valve 28 is mounted in the distal adapter 20D, the material of the socket part need not be designed to conform to the valve member. Additionally, since the inner surface of the seal plate is shaped to conform to the end of the residual limb, it can be worn in comfort without an inner socket part. Additionally, the O-ring 72 or the edge 70D seals the holes necessary for the screws 74, so suction can be maintained.

Obviously, numerous modifications and variations of the present invention are possible in light of the above teachings. It is therefore to be understood that the invention may be practiced otherwise than as specifically described herein.

What is claimed as new and is desired to be secured by Letters Patent of the United States is:

1. A distal adaptor secured to the distal end of a rigid socket part with a cavity into which a residual limb may be introduced and to a prosthetic limb, said distal adaptor having a portion configured for securement to a prosthetic limb, said distal adaptor further having an air valve positioned to communicate with the cavity so as to selectively permit air flow to or from the cavity, said air valve being located substantially entirely within said distal adaptor to be substantially on a longitudinal axis of said socket part.

2. The distal adaptor of claim 1 including a filter positioned for filtering air passing through said air valve from said cavity.

3. The distal adaptor of claim 1 wherein said air valve is a one-way valve mounted in a bore of said adaptor and permitting air flow from said cavity.

4. The distal adaptor of claim 1 wherein said air valve is a two-way air valve mounted in a bore of said adaptor and having a manually actuatable air release member.

5. The distal adaptor of claim 3 wherein said adaptor is a pyramid adaptor.

6. The distal adaptor of claim 3 wherein said adaptor is a pylon clamp adaptor.

7. The distal adaptor of claim 4 wherein said adaptor is a pyramid adaptor.

8. The distal adaptor of claim 4 wherein said adaptor is a pylon clamp adaptor.

9. The distal adaptor of claim 4 wherein said two-way air valve is mounted in a sleeve within said bore in said adaptor.

10. The distal adaptor of claim 1, including means for removably securing the distal adaptor to the socket part.

11. A distal adaptor comprising:
    an adaptor part secured to a distal end of a rigid socket part with a cavity into which a residual limb may be introduced and a seal plate mountable to the distal end of the socket part, said adaptor part having a portion configured for securement to a prosthetic limb, said distal adaptor further having:
    a securing element which secures said adaptor part to said seal plate; and
    an air valve mounted substantially entirely within said adaptor part to be substantially on a longitudinal axis of said socket part.

12. The distal adaptor of claim 11 wherein said seal plate has a surface which conforms in shape to the distal end of a residual limb to be inserted into said socket part.

13. The distal adaptor of claim 11 including a filter positioned for filtering air passing through said air valve from the cavity of the socket part.

14. The distal adaptor of claim 11 wherein said air valve is mounted to said seal plate.

15. The distal adaptor of claim 11 wherein said air valve is mounted to said adaptor part.

16. The distal adaptor of claim 11, wherein said adaptor part has a concave curved surface facing the interior of said socket part.

17. The adaptor of claim 11, including means for removably mounting the distal adaptor part to the socket part.

18. A distal adaptor securable to the distal end of a socket part with a cavity into which a residual limb may be introduced and to a prosthetic limb, said distal adaptor having a pyramid portion configured for securement to a prosthetic limb, said distal adaptor further having an air valve positioned to communicate with the cavity when the distal adaptor is secured to the distal end of the socket part so as to selectively permit air flow to or from the cavity, said air valve being located substantially entirely within said distal adaptor to be substantially on a longitudinal axis of said socket part when the distal adaptor is secured to the socket part.

19. A suspension system comprising a distal adaptor secured to the distal end of a rigid socket part having a cavity into which a residual limb may be introduced and to a prosthetic limb, said distal adaptor having a portion configured for securement to a prosthetic limb, said distal adaptor further having an air valve positioned to communicate with the cavity so as to selectively permit air flow to or from the cavity, said air valve being located substantially entirely within said distal adaptor to be substantially on a longitudinal axis of said suspension system.

20. A suspension system including a distal adaptor comprising an adaptor part secured to a distal end of a rigid socket part with a cavity into which a residual limb may be introduced and a seal plate mountable to the distal end of the socket part, said adaptor part having a portion configured for securement to a prosthetic limb, said distal adaptor further having:

a securing element which secures said adaptor part to said seal plate; and an air valve located substantially entirely within said adaptor part to be substantially on a longitudinal axis of said suspension system.

* * * * *

UNITED STATES PATENT AND TRADEMARK OFFICE
CERTIFICATE OF CORRECTION

PATENT NO. : 6,063,125
DATED : May 16, 2000
INVENTOR(S): Robert E. ARBOGAST et al.

It is certified that an error appears in the above-identified patent and that said Letters Patent is hereby corrected as shown below:

On the title page, item [45] is incorrectly listed. It should be:

--[45] Date of Patent: *May 16, 2000--

On the title page, the CPA information has been omitted. It should read as follows:

--[*] Notice: This patent issued on a continued prosecution application filed under 37 CFR 1.53(d), and is subject to the twenty year patent term provisions of 35 U.S.C. 154(a)(2)--

On the title page, item [54], and at the top of Column 1, the Title is incorrect. It should read as follows:

--[54] SUSPENSION FOR PROSTHETIC LIMBS--

Signed and Sealed this

Eighth Day of May, 2001

*Attest:*

NICHOLAS P. GODICI

*Attesting Officer*   Acting Director of the United States Patent and Trademark Office